US010258399B2

(12) United States Patent
Vogt et al.

(10) Patent No.: US 10,258,399 B2
(45) Date of Patent: Apr. 16, 2019

(54) PASTE APPLICATION SYSTEM FOR THE MIXING OF A PASTE MADE OF TWO COMPONENTS

(71) Applicant: HERAEUS MEDICAL GMBH, Wehrheim (DE)

(72) Inventors: Sebastian Vogt, Erfurt (DE); Clemens Greiner, Garbsen (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 107 days.

(21) Appl. No.: 14/863,569

(22) Filed: Sep. 24, 2015

(65) Prior Publication Data

US 2016/0082454 A1    Mar. 24, 2016

(30) Foreign Application Priority Data

Sep. 24, 2014    (DE) .................... 10 2014 113 816

(51) Int. Cl.
*B05B 9/03*       (2006.01)
*B05D 1/02*       (2006.01)
(Continued)

(52) U.S. Cl.
CPC .... *A61B 17/8822* (2013.01); *B05C 17/00559* (2013.01); *B05C 17/015* (2013.01);
(Continued)

(58) Field of Classification Search
CPC ............ A61B 17/8802; A61B 17/8822; A61B 17/8825; A61B 17/8827; B05C 17/00559;
(Continued)

(56) References Cited

U.S. PATENT DOCUMENTS

| 2,818,999 A | 1/1958 | Miller et al. |
| 4,690,306 A * | 9/1987 | Staheli .............. B05C 17/00513 222/137 |

(Continued)

FOREIGN PATENT DOCUMENTS

| DE | 3920694 A1 * | 1/1991 | .......... B01F 11/0085 |
| EP | 0 213 073 A1 | 3/1987 | |

(Continued)

OTHER PUBLICATIONS

European Search Report dated Feb. 11, 2016.

*Primary Examiner* — Nicholas J. Weiss
(74) *Attorney, Agent, or Firm* — Norris McLaughlin P.A.

(57) ABSTRACT

Paste application system having a two-component cartridge with two axially shiftable feed plungers; one hollow cylinder with an open front face and an at least partially closed front face, an axially mobile first plunger situated therein with two pestles attached to it; another hollow cylinder that contains a manually shiftable second plunger; and a liquid container, whereby the second hollow cylinder is connected or connectable to the liquid container in liquid-permeable manner by a first conduit means and a first non-return valve, and the first hollow cylinder is connected or connectable to the second hollow cylinder in liquid-permeable manner by a second conduit means and a second non-return valve; whereby the two-component cartridge and the first hollow cylinder, arranged axially adjacent, with the axially mobile pestles are arranged in a pressure container; and the paste application system contains a hollow space and liquid is present in said space.

22 Claims, 7 Drawing Sheets

(51) Int. Cl.
  *A61B 17/88* (2006.01)
  *B65D 81/32* (2006.01)
  *B05C 17/005* (2006.01)
  *B05C 17/015* (2006.01)

(52) U.S. Cl.
  CPC ....... *B65D 81/325* (2013.01); *B65D 81/3255* (2013.01); *B05C 17/0052* (2013.01)

(58) Field of Classification Search
  CPC ............ B05C 17/015; B05C 17/00543; B65D 81/3255; B65D 81/325
  See application file for complete search history.

(56) References Cited

U.S. PATENT DOCUMENTS

| | | | |
|---|---|---|---|
| 4,925,061 A * | 5/1990 | Jeromson, Jr. | ........ B05C 17/015 222/1 |
| 5,816,445 A * | 10/1998 | Gardos | ............... B01F 15/0454 222/1 |
| 6,582,446 B1 | 6/2003 | Marchosky | |
| 8,579,908 B2 | 11/2013 | Mazzuca et al. | |
| 2002/0000450 A1* | 1/2002 | Brown | .................. B05C 17/003 222/137 |
| 2011/0160737 A1 | 6/2011 | Steffen et al. | |

FOREIGN PATENT DOCUMENTS

| | | |
|---|---|---|
| EP | 1 118 313 A1 | 7/2001 |
| WO | 2007 028253 A2 | 3/2007 |

* cited by examiner

PASTE APPLICATION SYSTEM FOR THE MIXING OF A PASTE MADE OF TWO COMPONENTS

PRIORITY CLAIM

This application claims priority of German Patent Application No. 10 2014 113 816.3, filed on Sep. 24, 2014, the entire contents of which is incorporated herein by reference.

DESCRIPTION

The invention relates to a paste application system for storing two starting components, for mixing the starting components to form a paste, and for application of the paste.

The invention further relates to a method for mixing and dispensing a paste.

Accordingly, the object of the invention is a manually operated device (the paste application system) designed for dispensing pasty masses, in particular pasty polymethylmethacrylate cement dough (PMMA cement dough). The paste application system and the method are further intended for storing, mixing, and dispensing pasty two-component systems.

After mixing a cement powder, as the first starting component, with a liquid monomer component, as the second starting component, polymethylmethacrylate bone cements (PMMA bone cements) can be applied as a so-called cement dough in not-yet-cured pasty condition. If mixing systems are used with powder-liquid cements, the cement dough is situated in a cartridge. The cement dough is squeezed from said cartridge through the motion of a feed plunger. The motion of the feed plunger is effected by mechanical dispensation devices.

In the case of pasty two-component bone cements, both pasty components are stored in two separate cartridges with two separate feed plungers. During application, both pastes are pressed from the interior spaces of the cartridge into a static mixer through the motion of the feed plungers and are dispensed through a dispensing tube once the mixing is completed.

The application of pasty adhesives and sealants is done basically the same way using paste application systems.

Currently, paste application systems that can be driven manually or pneumatically or electrically are used to extrude thick viscous masses. Customary mechanical paste application systems utilise, in particular, clamp rods that are driven by a manually-operated tilting lever for extrusion.

Pneumatic paste application systems need to be connected to compressed air. This necessitates compressed air hoses, which may impede the mobility of the user and the use of the paste application system. Alternatively, the use of compressed gas cartridges to provide compressed gas is feasible just as well. Documents U.S. Pat. No. 2,818,999 and EP 1 118 313 A1 shall be cited as being exemplary in this context.

Electrically-driven extrusion devices can be driven both with rechargeable batteries and/or batteries or by means of a stationary electrical power supply. Said devices can extrude particularly thick pasty masses since their force is very large in some cases. However, it is one disadvantage of the use of electrical motors that these motors are expensive and contain non-ferrous metals. Moreover, strong motors and their energy reservoirs are usually heavy and inconvenient to handle.

U.S. Pat. Nos. 6,582,446 B1, 8,579,908 B2, WO 2007/028253 A2, and US 2011/0160737 A1 disclose hydraulic devices that are intended for the dispensation of bone cement for vertebroplasty and kyphoplasty, i.e. the augmentation of fractured vertebral bodies with polymethylmethacrylate bone cement. Only small volumes of just a few cubic centimetres of bone cement are required to fill fractured vertebrae. For this reason, the devices described in these documents are designed to dispense small cement volumes only. In the known hydraulic devices, the application of the cement is preceded by mixing the powdered component and the liquid monomer component outside of the hydraulic device, and the bone cement dough thus formed is subsequently filled into the application device. Vertebroplasty and kyphoplasty are both performed under continuous radiological monitoring. In order to prevent unnecessary exposure of the attending physician to radiation, the build-up of pressure by the physician proceeds spatially separated from the dispensation of the cement. For this purpose, a handle with the pump plunger is connected to the applicator by means of a flexible tubing. This allows the physician to operate the applicator from outside the x-ray beam without being exposed to radiation. The system must be configured with ready-mixed bone cement. Moreover, more substantial amounts of bone cement cannot be used with the system. The known paste application systems may fail in the case of very thick paste mixtures.

It is the object of the invention to overcome the disadvantages of the prior art. Specifically, a paste application system and a method for mixing and dispensing of the paste are to be found by means of which even a very viscous mass can be stored, mixed, and dispensed using a simple design. In this context, the paste application system shall be inexpensive enough to enable its single use (disposable article). Disposable articles are advantageous in surgical theatres due to the existing strict hygienic requirements.

Moreover, one object of the invention is to provide a paste application system and a method that can be driven without the use of external stationary energy sources, such as compressed air or electrical current, and that are able to extrude viscous pasty masses. Moreover, the device shall contain no internal energy sources, such as rechargeable batteries, batteries or compressed gas cartridges. In addition, the dispensing device shall contain no copper and no copper alloys. It shall be feasible for the user to drive the dispensing device manually from any location. The design of the dispensing device is to be as simple as possible. The aim is to enable the provision of an inexpensive dispensing device that is intended for single use only. Moreover, it is another object of the invention to develop a method for the dispensing of pasty masses by means of the dispensing device to be developed.

The object of the invention can also be seen to be to develop a compact paste application system, in which the mixing of viscous cement pastes by means of a static mixer is made feasible by driving it manually. Moreover, it shall be feasible to store two cement pastes separately in the paste application system before applying the cement. The system must allow for manually-driven dispensation of at least 40 g to 75 g of mixed cement paste. Moreover, it must be feasible to sterilise the surface of the paste application system with ethylene oxide. It is important that the high-pressure required during the application does not lead to undesired leakage of cement, which might lead to contamination of the medical user and surgical theatre (OR room). It should be possible to manually operate the paste application system with as little force as possible. Another important point for application is that no substantial amounts of the cement dough and/or paste continue to flow out when the dispensation of cement is discontinued.

The objects of the invention are met by a paste application system for storing two starting components, for mixing the starting components to form a paste, and for application of the paste, comprising a two-component cartridge with two axially shiftable feed plungers;

a first hollow cylinder with an open front face and an at least partially closed front face, in which is situated an axially mobile first plunger with two pestles attached to it that is arranged appropriately such that the open front face touches axially on the two-component cartridge;

a second hollow cylinder that contains a manually shiftable second plunger; and a liquid container, whereby the second hollow cylinder is or can be connected to the liquid container in liquid-permeable manner by means of a first conduit means and by means of a first non-return valve, and the first hollow cylinder is or can be connected to the second hollow cylinder in liquid-permeable manner by means of a second conduit means and by means of a second non-return valve;

whereby the two-component cartridge and the first hollow cylinder, arranged axially adjacent, with the axially mobile pestles are arranged in a pressure container; and whereby a hollow space for the liquid is formed in the paste application system by the liquid container, the first conduit means, the second conduit means, the first non-return valve, the second non-return valve, the internal space of the first hollow cylinder that is bordered by the first plunger and the internal space of the second hollow cylinder that is bordered by the second plunger, and whereby a liquid is present in the hollow space for the liquid or can be filled into the hollow space for the liquid.

The liquid should be incompressible and at least largely devoid of gas inclusions to allow for good hydraulic transmission of a pressure by the liquid and to prevent substantial amounts of the mixed paste, in particular of the bone cement, from continuing to flow after discontinuation of the propulsion, because compressed gas inclusions expand once the pressure built-up manually is no longer applied. As a matter of rule, all liquids that can flow at 23° C. and normal pressure can be used as liquids. In this context, gels that can flow and are stable in volume, but not stable in shape, can be used just as well Water, water-containing polymer gels, low molecular polyethylene glycol, low molecular polypropylene glycol, paraffin, and silicon oils are preferred as liquids. Polymer-thickened aqueous solutions having a melting point below −10° C. are particularly preferred. Glycerol, 1,2-ethylene glycol, 1,2-propylene glycol, 1,3-propylene glycol, 1,4-butandiol, diethylene glycol, triethylene glycol, and tetraethylene glycol can be added as additives to lower the melting point of the liquid. In addition, any other non-toxic and non-corrosive liquids or easily flowing gels or gel particle suspensions that have a melting point below −10° C., particularly preferably of −20° C., and even more particularly preferably of −30° C., are conceivable as liquids.

A non-return valve shall be understood to be any form of valve that opens in a first flow direction and closes in an opposite second flow direction, such as, for example, check valves or spring-loaded check valves. Particularly preferred in this context are non-return ball valves with conical seat or ball seat, in which a ball is pressed onto the seat by means of a tensioned compression spring, whereby the compression spring can be compressed further by means of a liquid flow and/or a liquid pressure, causing the ball to detach from the seat and thus open the valve as long as a liquid of sufficient pressure flows through the non-return ball valve. With the flow being opposite, the non-return ball valve closes, since the liquid pressure and the compression spring press the ball into the seat, which closes the opening that is present in the seat.

All liquid conduits that are resistant to the pressure of the liquid to be conducted can be used as conduit means. Accordingly, pressure-stable hydraulic conduits, in particular, are preferred in this context.

A two-component cartridge comprises at least two cartridge interior spaces for two starting components of the paste. The two-component cartridge can just as well comprise further cartridge interior spaces for the two components or for additional third components. Accordingly, a three-component cartridge would comprise a two-component cartridge according to the spirit of the present invention. Likewise, a two-component cartridge according to the invention can contain more than two feed plungers and, accordingly, more than only two pestles can be attached to the first plunger to drive the feed plungers without deviating from the scope of the present invention. A person skilled in the art recognises the underlying principle and can easily apply it to a larger number of cartridges, feed plungers, hollow cylinders, valves, conduits, and pestles without deviating from the idea underlying the invention.

When the paste application system is in the storage state, the liquid container, the first conduit means, the second conduit means, the second hollow cylinder, and the not-yet-expanded second hollow space of the first hollow cylinder are not necessarily filled with liquid yet. The liquid can be added prior to the use of the paste application system. However, it is feasible just as well that the liquid is already present in the paste application system.

The paste application system according to the invention is intended and well-suited for the dispensation of polymethylmethacrylate bone cement, adhesives, and sealants, and can be used to dispense any pasty masses.

Preferably, the first hollow cylinder and the second hollow cylinder are made from polyamide, polyether amide, polyimide, polyethersulfone, polyketone or glass fibre-reinforced composites of said polymers. In addition, it is feasible just as well to produce the first hollow cylinder and the second hollow cylinder from aluminium or aluminium alloys. Depending on the specific application, the internal walls of the two-component cartridge should be coated by a special plastic material, if applicable, that prevents the starting components and the material of the cartridges from undergoing a chemical reaction. The first and the second conduit means can consist of fabric-reinforced elastomer or of aluminium or aluminium alloys as well. The remaining components of the dispensing device preferably consist of common technical plastic materials except for the pressure container.

The liquid container preferably has a larger volume than the first hollow cylinder.

The pressure container is preferably cylindrical in shape in order to take up the acting forces well. Preferably, the internal space of the pressure container comprises cylindrical regions. The shape of the pressure container, at least of regions thereof, must be adapted to the external shape of the two-component cartridge and the external shape of the first hollow cylinder in order to take up the acting forces well.

In paste application systems according to the invention, the invention can just as well provide the paste application system to comprise a dispensing tube with an integrated static mixer that is arranged on or can be attached to the end of the two-component cartridge opposite from the feed plungers.

Preferably, the dispensing tube can be screwed into and/or attached to the front end of the two-component cartridge in place of a closure, whereby the closure separates the two starting components from each other. For this purpose, the closure preferably is a part of the walls of the internal spaces of the cartridge such that the contents of the internal spaces of the cartridge can be mixed with each other, when the closure is taken out and/or removed.

Moreover, the invention can provide the pressure container to have a tensile modulus in accordance with EN ISO 527 of more than 1,500 MPa.

As a result, it can be ensured that the pressure container can take up the pressures required for extruding and mixing of viscous PMMA bone cements without being destroyed.

A further development of the paste application system also proposes the liquid container to comprise a volume compensation element, preferably to comprise an axially shiftable third plunger as volume compensation element.

As a result, no negative pressure is built up in the liquid container when liquid is being pumped from the liquid container into the first hollow cylinder. A negative pressure in the liquid container would have a disadvantageous effect, since the pump motion would have to perform additional work.

In this context, the invention can provide a tensioned compression spring to be arranged on the side of the volume compensation element of the liquid container that faces away from the region for the liquid, in particular on the third plunger, and to push the volume compensation element in the direction of the liquid container, in particular to move the third plunger axially in the liquid container, and to press liquid through the first conduit means and through the first non-return valve to the second hollow cylinder.

As a result, no additional force is required to transport the liquid from the liquid container into the second and the first hollow cylinder.

A refinement of the invention also proposes to provide an opening in the jacket surface of the pressure container that is connected, in gas-permeable manner, to an opening in the first hollow cylinder such that the space between the two-component cartridge and the axially mobile pestles is connected to the ambient atmosphere in gas-permeable manner.

This prevents an over-pressure from being formed, when the pestles and the first plunger are propelled forward in the first hollow cylinder, and from counteracting the propulsion of the pestles and/or first plunger.

According to a preferred embodiment of the paste application system, the invention can just as well provide at least one closable opening for the addition of liquid that is connected to the hollow space for the liquid that is formed by the liquid container, the first conduit means, the second conduit means, the first non-return valve, the second non-return valve, the interior space of the first hollow cylinder bordered by the first plunger and the interior space of the second hollow cylinder bordered by the second plunger, whereby the opening for the addition of liquid is preferably arranged on the liquid container.

This can ensure that the entire hydraulic system can easily be filled with a liquid.

Moreover, the invention can just as well provide at least one closable ventilation opening that is connected to the hollow space for the liquid that is formed by the liquid container, the first conduit means, the second conduit means, the first non-return valve, the second non-return valve, the interior space of the first hollow cylinder bordered by the first plunger and the interior space of the second hollow cylinder bordered by the second plunger.

The ventilation opening can ensure that as little air as possible remains in the liquid, where it would interfere with the propulsion of the pestles and thus of the paste.

In this context, the invention can provide the closed front face of the first hollow cylinder to be curved and the closable ventilation opening to be arranged in the curvature.

Any air inclusions accumulate in said curvature such that the air inclusions can be removed particularly easily at this site.

The invention can just as well provide the two-component cartridge, the first hollow cylinder, and the second hollow cylinder to be arranged in a housing, whereby it is preferred to have the first conduit means, the first non-return valve, the second conduit means, and the second non-return valve also be arranged in said housing.

As a result, the entire paste application system can be operated and held in one hand as one unit. Any moving parts are thus closed off from the exterior such that no inadvertent blockage of moving parts can occur.

Preferred paste application systems can be characterised in that the liquid is present without any visually recognisable gas bubbles in the hollow space for the liquid and/or in that the liquid contains less than 5% by volume of gas, preferably less than 1% by volume of gas.

By this means, it can be ensured that no compressible gas bubbles or air inclusions are present in the liquid, which would, on the one hand, take up force undesirably and without utilising it and, on the other hand, would expand when the force ceases to act and thus cause the paste to continue to flow without a force being manually applied to the paste application system and without further dispensation being desired.

To take up the arising forces, the invention can provide the distances between the pressure container and the external wall of the two-component cartridge and between the pressure container and the external wall of the first hollow cylinder to be smaller than 100 μm, preferably to be smaller than 50 μm. Said distances do not have to be as specified across their entire surface area, rather it may be sufficient if the distances are as specified over regions thereof, depending on the nature of the two-component cartridge and of the first hollow cylinder.

This ensures that the first hollow cylinder and the two-component cartridge cannot become strongly deformed by the very high hydraulic pressure, since the pressure container is touching or close to touching them and can therefore take up all shear and torsional forces. In the absence of this measure, the two-component cartridge and the first hollow cylinder cannot be made from simple plastic material and/or with low wall thickness.

Preferred paste application systems can provide the pressure container to be made from a material selected from aluminium, aluminium alloys, and high-performance plastics. Particularly preferred paste application systems can provide the pressure container to be made of a material selected from duroplasts, polyamides, polyamide-co-imides, polysulfones, polyketones, and polyetherketones. The latter plastics are considered to be high-performance plastics.

As a result, a sufficient stability of the pressure container is attained through the selection of material.

In a reusable refinement of the paste application system according to the invention, the invention can provide a liquid-permeable third conduit means and a third valve, which can be closed reversibly by hand, to connect the first hollow cylinder to the liquid container. Preferably, the hollow space between the first plunger and the rear wall of the first hollow cylinder is connected to the liquid container by means of the third conduit means and the third valve.

As a result, the liquid can be pressed back from the first hollow cylinder into the liquid container after application of the paste application system by pushing the pestles with the first plunger back into the first hollow cylinder. Accordingly, this design renders the paste application system reusable. For this purpose, the empty two-component cartridge can simply be taken out of the paste application system and/or out of the pressure container of the paste application system and can be replaced by a filled two-component cartridge.

The invention can just as well provide that the surface area ratio of the front face of the first plunger and the front face of the second plunger is at least 10 to 1, preferably is at least 20 to 1, particularly preferably is at least 30 to 1.

The kind of transmission ratio allows a strong force to be transmitted by means of which even very viscous pastes can be expelled from the paste application system and/or the components and/or paste can flow through very strong mixers.

Moreover, the invention can provide the two-component cartridge to comprise two interior spaces of the cartridge, whereby the feed plungers are axially mobile in the interior spaces of the cartridge, whereby it is preferred that a first interior space of the cartridge surrounds a second interior space of the cartridge in coaxial manner.

As a result, the two components are stored in two separate interior spaces of the cartridge. The coaxial arrangement is a particularly stable configuration for the arising pressures. Side-by-side cartridges can be used just as well instead of the coaxial arrangement. For this purpose, the shape of the pressure container must be adapted to the shape of the two-component cartridge.

The invention can provide the interior spaces of the cartridge to be separated or separable on the side opposite from the feed plungers by means of a manually detachable closure, whereby the closure preferably is or can be screwed into an internal thread on the front side of the two-component cartridge.

By this means, the paste application system is also quite useful for the storage of the starting components of a PMMA bone cement, since the starting components thereof need to be stored strictly separate from each other, since a chemical reaction would otherwise lead to premature curing of the cement which would render the paste application system useless.

The invention also proposes the pressure container to comprise at least one opening each on the front faces, whereby it is preferred to have at least one valve for gas release arranged on one of the openings.

The first opening is designed for dispensation of the paste, and the at least one other opening on the opposite front face is designed for the release of air from the liquid and/or for guiding the liquid.

The objects underlying the invention are also solved through a method for mixing and dispensing a paste comprising the steps of:

guiding a liquid from the liquid container through the first non-return valve and the first conduit means into the second hollow cylinder;

subsequently, pushing the liquid from the second hollow cylinder through the second non-return valve and the second conduit means into the first hollow cylinder by applying a manual pressure on the second plunger in the second hollow cylinder, whereby the liquid pressed into the first hollow cylinder pushes the first plunger, which has a larger face surface to the liquid as compared to the second plunger, in the direction of the two-component cartridge, whereby at least the two feed plungers that are axially shiftable in the two-component cartridge are propelled by the first plunger or by the pestles attached to the first plunger in at least two interior spaces of the two-component cartridge, whereby the content is expelled from the two-component cartridge and is subsequently mixed and is applied after the mixing.

Preferably, the method can also be well-suited for storage of the starting components. For this purpose, the invention can provide the closure to be inserted into the two-component cartridge while the starting components are being stored, whereby the at least two starting components are separated from each other by the closure, and the closure to be removed prior to the use of the paste application system. Preferably, a dispensing tube through which the paste is applied is inserted into the two-component cartridge in place of the closure.

The invention can provide for the use of a paste application system according to the invention for implementation of the method.

The invention can just as well provide the forces, which occur when the liquid is pressed into the first hollow cylinder and when the first plunger and the feed plungers are propelled in the two-component cartridge, to be taken up by a pressure container that surrounds the two-component cartridge and the first hollow cylinder, preferably touches against the two-component cartridge and the first hollow cylinder. The pressure container is preferred to be essentially cylindrical. The pressure container preferably comprises an interior space, regions of which are cylindrical.

Moreover, the invention can provide the second hollow cylinder to be filled repeatedly with the liquid from the liquid container by restoring the second plunger, whereby the restoration of the second plunger preferably is effected by means of a compression spring that gets tensioned when the second plunger is being pushed in, or by any other restoring element.

The invention can just as well provide the first non-return valve to be opened and the second non-return valve to be closed, when the liquid is guided from the liquid container into the second hollow cylinder, and the first non-return valve to be closed and the second non-return valve to be opened when the liquid is pressed from the second hollow cylinder into the first hollow cylinder.

The invention is based on the surprising finding that the design according to the invention allows to provide a manually-driven paste application system that is sufficient for hydraulic use, has a compact and inexpensive design, and, in addition, is well-suited for storing the cement components.

Usually, 40 g to 75 g of bone cement are needed for implantation of artificial knee and hip joints. Own experiments, in which 60 g each of two cement pastes were mixed to form a cement dough in a dispensing tube with an internal diameter of 9 mm through the use of a static mixture, showed that very high pressures of 25 bar to 45 bar are required to move the cement pastes through the static mixer. The results of own experiments with plastic cartridges and plungers that are axially mobile in the cartridges demonstrated that the plastic cartridges show clear signs of deformation when exposed to pressures in excess of 25 bar. These deformations lead to leakiness between the internal surface of the cartridges and the feed plungers despite the use of elastic sealing rings. As a result, pasty material might leak out. For this reason, a preferably cylindrical pressure container is proposed, according to the scope of the present invention, that surrounds the two-component cartridge and the first hollow cylinder and is capable of taking up the mechanical loads.

In further experiments, it was found that it is very difficult to store cement cartridges appropriately during the dispensation of the cement pastes, during the propulsion of the feed plungers by pestles, such that the cement cartridges do not move away from the pestles and the pestle drive due to deformation or twisting at internal pressures in excess of 20 bar. Own experiments further showed that cement cartridges made of aluminium alloys are unsuitable for polymethylmethacrylate cement pastes, since the alloys and the alloy ingredients present in them, such as copper and manganese, effect an undesired radical polymerisation during the storage of cement pastes in the cement cartridge. Polymethylmethacrylate-containing cement pastes are long-term stable on storage only in cement cartridges made from suitable plastic materials, such as poly-acrylonitrile-co-methylmethacrylate and polybutylene terephthalate.

A general exemplary embodiment of the invention shall be described in the following.

An exemplary paste application system is composed of a two-component cartridge with two axially shiftable plungers, a dispensing tube with integrated static mixer, a first hollow cylinder with an open front side and a closed front side, in which an axially mobile first plunger with two pestles attached to it is situated, a second hollow cylinder that contains a manually shiftable second plunger, a liquid container with an axially shiftable feed plunger, whereby the liquid container is connected to the second hollow cylinder in liquid-permeable manner by means of a first conduit means and by means of a first non-return valve, and the second hollow cylinder is connected to the first hollow cylinder in liquid-permeable manner by means of a second conduit means and a second non-return valve.

In this context, the two-component cartridge and the hollow cylinder with axially mobile pestles that is arranged axially downstream from the two-component cartridge are arranged in a cylindrical pressure container with a tensile modulus according to ISO 527 of more than 1,500 MPa, whereby the pressure container has at least one opening at each of the front faces, and one opening is arranged appropriately on the jacket surface such that the hollow space between the two-component cartridge and the axially mobile pestles is connected to the ambient atmosphere in gas-permeable manner.

Moreover, the invention provides at least one closable opening for the addition of the liquid that is connected to the hollow space formed by the liquid container, the first conduit means, the first non-return valve, the first hollow cylinder with the first plunger, the second conduit means, the second non-return valve, the second hollow cylinder, and the second plunger.

Moreover, the invention can provide for arrangement of at least one closable ventilation opening that is connected to the hollow space formed by the liquid container, the first conduit means, the first non-return valve, the first hollow cylinder with the first plunger, the second conduit means, the second non-return valve, the second hollow cylinder, and the second plunger.

Moreover, the invention can provide for arranging a liquid without visually recognisable gas bubbles in the hollow space formed by the liquid container, the first conduit means, the first non-return valve, the first hollow cylinder with the first plunger, the second conduit means, the second non-return valve, the second hollow cylinder, and the second plunger.

Moreover, the invention can provide the two-component cartridge, the first hollow cylinder with the first plunger and pestles, the first conduit means, the first non-return valve, the second hollow cylinder, the second plunger, the second conduit means, the second non-return valve to be arranged in a housing.

The exemplary paste application system provides the distances between the pressure container and the external wall of the two-component cartridge and between the pressure container and the external wall of the first hollow cylinder to be smaller than 100 μm.

The pressure container can preferably be made from aluminium or aluminium alloys or high-performance plastics in this context, whereby polyamides, polyamide-co-imides, polysulfones, polyketones, and polyetherketones are particularly preferred. The closed front face of the first hollow cylinder is curved and the closable ventilation opening is arranged in the curvature such that air inclusions that might be present in the liquid after the filling process can be released easily. For this purpose, the opening for the addition of liquid is preferably arranged on the liquid container.

A tensioned spring is arranged behind the plunger of the liquid container and moves the plunger axially in the liquid container and presses liquid through the first conduit means and through the first non-return valve to the second hollow cylinder. A liquid-permeable third conduit means and a reversibly closable third valve can connect the hollow space in the first hollow cylinder to the liquid container in order to be able to press the liquid back from the first hollow cylinder into the liquid container using the first plunger and to thus render the paste application system reusable and/or ready for another use. In this case, it is only necessary to insert a new filled two-component cartridge.

In order to obtain the pressure required for extrusion, the invention provides the surface area ratio of the front surface area of the first plunger to the front surface area of the second plunger to be at least 20 to 1, and preferably to be more than 30 to 1.

BRIEF DESCRIPTION OF THE DRAWINGS

Further exemplary embodiments of the invention shall be illustrated in the following on the basis of seven schematic figures, though without limiting the scope of the invention. In the figures:

FIG. 3: shows a schematic cross-sectional view of a part of the paste application system according to FIG. 2 with a closure screwed in;

FIG. 5: shows a schematic perspective view of the paste application system according to FIGS. 2 to 4 with a closure screwed in;

FIG. 6: shows a schematic perspective view of the paste application system according to FIGS. 2 to 5 with a dispensing tube screwed in.

Identical or similar components are identified in the figures, to some extent, through the same reference numbers even if different paste application systems are concerned.

Figure 1:
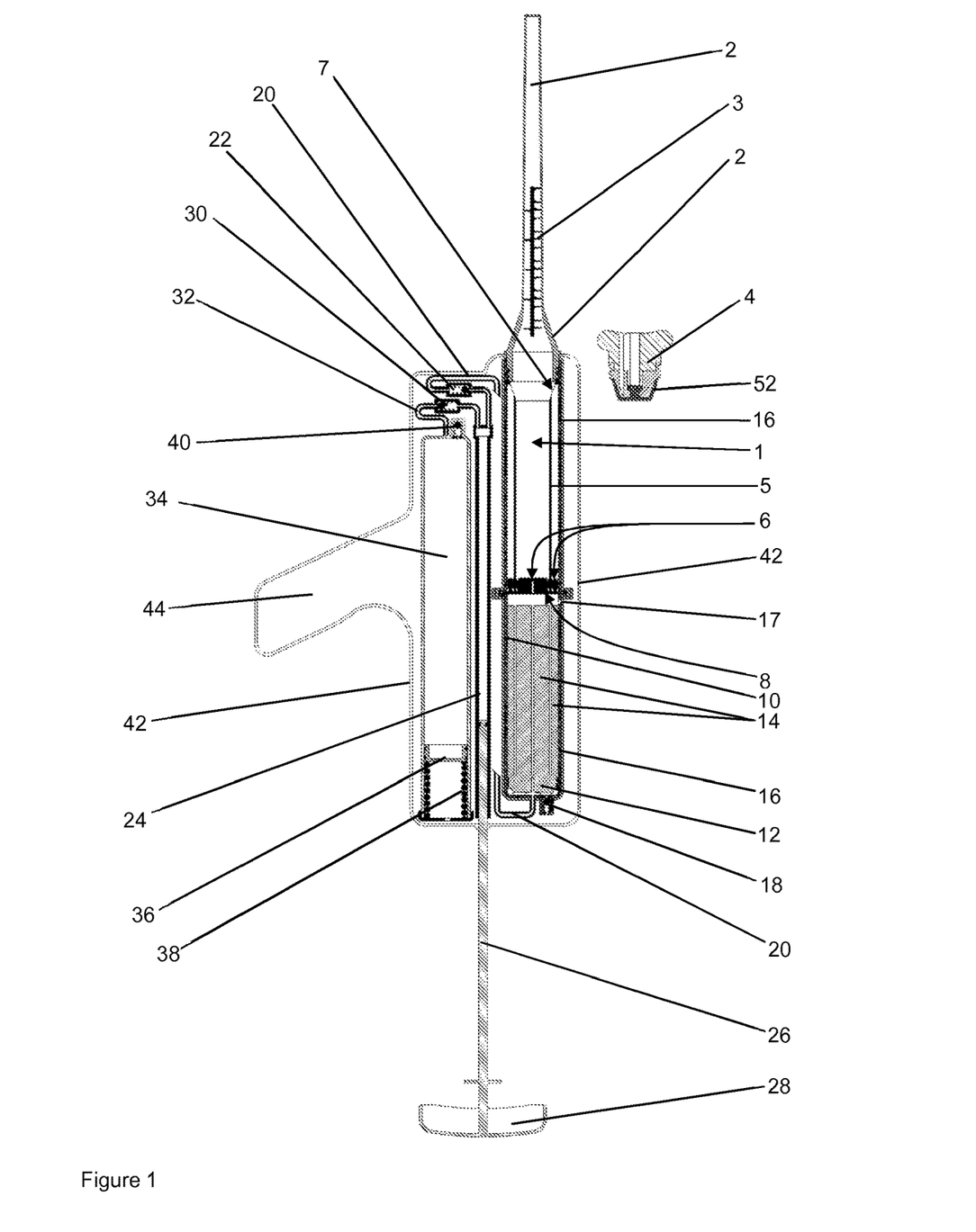
FIG. 1: shows a schematic cross-sectional view of a paste application system according to the invention.

FIG. 1 shows a schematic cross-sectional view of a paste application system according to the invention. The paste application system has a two-component cartridge 1 that contains two pasty starting components (not shown) for the production of a polymethylmethacrylate bone cement (PMMA bone cement) in interior spaces of the cartridge that are separated from each other and are arranged coaxially with respect to each other. A dispensing tube 2, in which a static mixer 3 is arranged, is attached on the front side of the two-component cartridge 1. In the storage state of the paste application system, a closure 4 is inserted into the front end (on the top in FIG. 1) of the two-component cartridge 1 in place of the dispensing tube 2.

For separation of the interior spaces of the two-component cartridge 1, a cylindrical tube is provided as a separating wall 5 between the two interior spaces of the cartridge. This results in an outer interior space of the cartridge that is separated from the inner interior space of the cartridge by the cylindrical separating wall 5. The rear-side end (on the bottom in FIG. 1) of the two-component cartridge 1 has two feed plungers 6 arranged in the interior spaces of the cartridge, which are arranged such as to be axially mobile in the interior spaces of the cartridge and are sealed with respect to the bordering walls 5, 1 of the interior spaces of the cartridge by means of sealing rings. The interior spaces of the cartridge are connected to each other by means of openings 7 on the front side (on the top in FIG. 1) such that the interior spaces of the cartridge merge into each other toward the dispensing tube 2. The two-component cartridge 1, the dispensing tube 2, and the separating wall 5 can be made of a plastic material that is chemically resistant to the content of the cartridge.

The two-component cartridge 1 is closed on its rear side by means of a film 8 made of plastic material, which closes the two-component cartridge 1 in gas-tight manner, when the closure 4 is inserted in the two-component cartridge 1 and closes the openings 7.

A hollow cylinder 10 is placed against the rear side of the two-component cartridge 1 and is closed on the rear side (on the bottom in FIG. 1) in pressure-tight manner by means of a plunger 12. The plunger 12 is sealed with respect to the wall of the hollow cylinder 10 by means of seals and is axially mobile in the hollow cylinder 10. The plunger 12 is extended in pestles 14 that comprise recesses or free regions at least in one region, whereby the recesses are required to be able to propel the pestles 14 into the interior spaces of the cartridge, i.e. to take up the separating wall 5.

Driven forward, the pestles 14 sever the film 8 and drive the feed plungers 6 in the direction of the dispensing tube 2, which expels the content of the two-component cartridge from the interior spaces of the cartridge, presses them into the mixer 3, where the two starting components are mixed with each other, and the mixed paste can be applied by means of the tip of the dispensing tube 2.

For this purpose, the plunger 12 must be driven forward (upward in FIG. 1) at a high pressure due to the high viscosity of the starting components and mixed paste and due to the resistance exerted by the static mixer 3. Since the hollow cylinder 10 also consists of a plastic material, the hollow cylinder 10 and the two-component cartridge 1 must be protected from the very strong forces required. For this purpose, the two-component cartridge 1 and the hollow cylinder 10 are surrounded by a pressure container 16 made of metal or a very tough plastic material, such as, e.g., duroplasts, polyamides, polyamide-co-imides, polysulfones, polyketones, and polyetherketones. The pressure container 16 is capable of taking up a tensile modulus according to EN ISO 527 of more than 1,500 MPa. The pressure container 16 is designed to consist of two parts, whereby the two parts of the pressure container 16 are connected to each other, for example by means of a thread. The pressure container 16 is cylindrical on the inside and is placed, on the outside, against the two-component cartridge 1 and the hollow cylinder 10 or is situated at only a very small distance of maximally 100 μm from the two-component cartridge 1 and the hollow cylinder 10. This ensures that the two-component cartridge 1 and the hollow cylinder 10 are not deformed at all or only to a minor extent during the propulsion of the plunger 12 such that the moving parts, namely the plunger 12, the pestles 14, and the feed plungers 6, do not get lodged and blocked and such that no paste can leak out other than through the dispensing tube 2.

Openings 17, through which the air from the gap in the hollow cylinder 10 between the plunger 12 and/or the pestles 14 and the film 8 can escape, are provided on one side surface in the hollow cylinder 10 and the pressure container 16. This is meant to prevent the enclosed gas from counteracting the motion of the plunger 12. A manually operable valve 18, by means of which gas can be released from the space between the closed rear wall of the hollow cylinder 10 and the plunger 12, is provided on the rear side of the hollow cylinder 10 and of the pressure container 16. This allows a gas to be released from the hydraulic liquid. For this purpose, it is preferable to arrange the opening for the valve 18 on a curvature (not shown) such that the air or other gas inclusions collect(s) in the curvature and can be released by means of the valve 18, when the paste application system is held with the dispensing tube 2 facing downward.

Moreover, a hydraulic conduit 20 merges into the rear side of the hollow cylinder 10. A non-return valve 22 is arranged in the hydraulic conduit 20. The non-return valve 22 is designed to include a ball that is seated by means of a compression spring, whereby the ball is pressed onto a fitting ball seat by the compression spring in order to close the non-return valve 22. If the liquid contained therein flows in the direction of the hollow cylinder 10 at a sufficient pressure, the non-return valve 22 opens.

The hydraulic conduit 20 merges into a hollow cylinder 24, in which a plunger 26 that is supported such as to be axially mobile is arranged. The plunger 26 is sealed with respect to the internal walls of the hollow cylinder 24 through a sealing ring. The plunger 26 ends in a handle 28 by means of which the plunger 26 can be pushed into and pulled out of the hollow cylinder 24 by hand. When the plunger 26 is pushed into the hollow cylinder 24, the liquid present in the hollow cylinder 24 is pressed through the hydraulic conduit 20 and the non-return valve 22 into the hollow cylinder 10. Since the front surface area of the plunger 26 is significantly smaller than the corresponding front surface area of the plunger 12 (the front surface area of the plunger 26 is smaller than the front surface area of the plunger 12 by at least a factor of ten or a factor of twenty), this produces a transmission ratio. By this means, even a small force exerted by pressing on the plunger 26 can apply a large pressure on the plunger 12 which drives the feed plungers 6 such that very viscous pastes can be expelled and mixed.

The hollow cylinder 24 merges, on its front side, in a conduit 32 as well, in which a non-return valve 30 is arranged that is designed like the other non-return valve 22 in the hydraulic conduit 20. The non-return valve 30 permits the liquid to flow only in the direction of the hollow cylinder 24. The conduits 20, 32, the non-return valves 22, 30, and the connectors must be able to take up the high pressures that occur during operation, without becoming leaky.

On the other side, the conduit 32 merges into a cylindrical liquid container 34 that has a large volume as compared to the second hollow cylinder 24 and is closed, on one side, by means of a plunger 36 that is axially mobile and sealed. The plunger 36 is tensioned by means of a compression spring 38 such that the liquid can be easily pushed and/or drawn from the liquid container 34 into the conduit 32 and into the hollow cylinder 24 by the plunger 36. Retracting the plunger 26 generates a negative pressure in the hollow cylinder 24 such that the non-return valve 30 opens and the liquid can flow from the liquid container 34 into the hollow cylinder 24.

Accordingly, the plunger 12 is propelled forward in stages in hollow cylinder 10 by multiply pumping and/or by multiply pushing and retracting the plunger 26 in the hollow cylinder 24.

On the rear side (on the bottom in FIG. 1), an opening is provided in a cap of the liquid container 34 such that no negative pressure can build up between the plunger 36 and the cap and counteract a propulsion of the plunger 36. A non-return valve 40, by means of which the liquid container 34 can be filled with liquid, is provided on the front side of the liquid container 34.

The hollow cylinders 10, 24, the liquid container 34, the two-component cartridge 1, the conduits 20, 32, and the non-return valves 22, 30 are arranged in a housing 42 made of plastic material. The housing 42 forms a pistol handle 44 allowing the paste application system to be held. The handle 28, the valve 18, and the valve 14 project from the housing 42 and/or are accessible from outside the housing 42.

The closure 4 comprises seals 52 in the form of fitting surfaces that close the openings 7 in fluid-tight manner and thus reliably separate the contents of the interior spaces of the cartridge from each other. The closure 4 is removed from the front side of the two-component cartridge 1 right before the paste application system is used and, in place of the closure 4, the dispensing tube 2 is attached in the mounting previously used to mount the closure 4. Preferably, the mounting on the two-component cartridge 1 is a thread that engages a counter-thread on the closure 4 or a counter-thread on the dispensing tube 2. A force-locked placement of the seals 52 on the openings 7 of the two-component cartridge 1 can be attained by means of the thread.

FIGS. 2 to 6 show various schematic views of a second paste application system according to the invention that has a slightly different design. The paste application system has a two-component cartridge 1 that contains two pasty starting components (not shown) for the production of a PMMA bone cement in interior spaces of the cartridge that are separated from each other and are arranged coaxially with respect to each other. A dispensing tube 2, in which a static mixer 3 is arranged, is attached on the front side of the two-component cartridge 1 in FIGS. 2, 4, and 6. In the storage state of the paste application system shown in FIGS. 3 and 5, a closure 4 is inserted into the front end (as shown on the top in FIG. 1) of the two-component cartridge 1 in place of the dispensing tube 2.

For separation of the interior spaces of the two-component cartridge 1, a cylindrical tube is provided as a separating wall 5 between the two interior spaces of the cartridge. This results in an outer interior space of the cartridge that is separated from the inner interior space of the cartridge by the cylindrical separating wall 5. The rear-side end (on the bottom in FIGS. 2 to 6) of the two-component cartridge 1 has two feed plungers 6 arranged in the interior spaces of the cartridge, which are arranged such as to be axially mobile in the interior spaces of the cartridge and are sealed with respect to the bordering walls 5, 1 of the interior spaces of the cartridge by means of sealing rings.

The interior spaces of the cartridge are connected to each other by means of openings 7 on the front side (on the top in FIG. 2) such that the interior spaces of the cartridge merge into each other toward the dispensing tube 2. The two-component cartridge 1, the dispensing tube 2, and the separating wall 5 can be made of a plastic material that is chemically resistant to the content of the cartridge.

Figure 2:
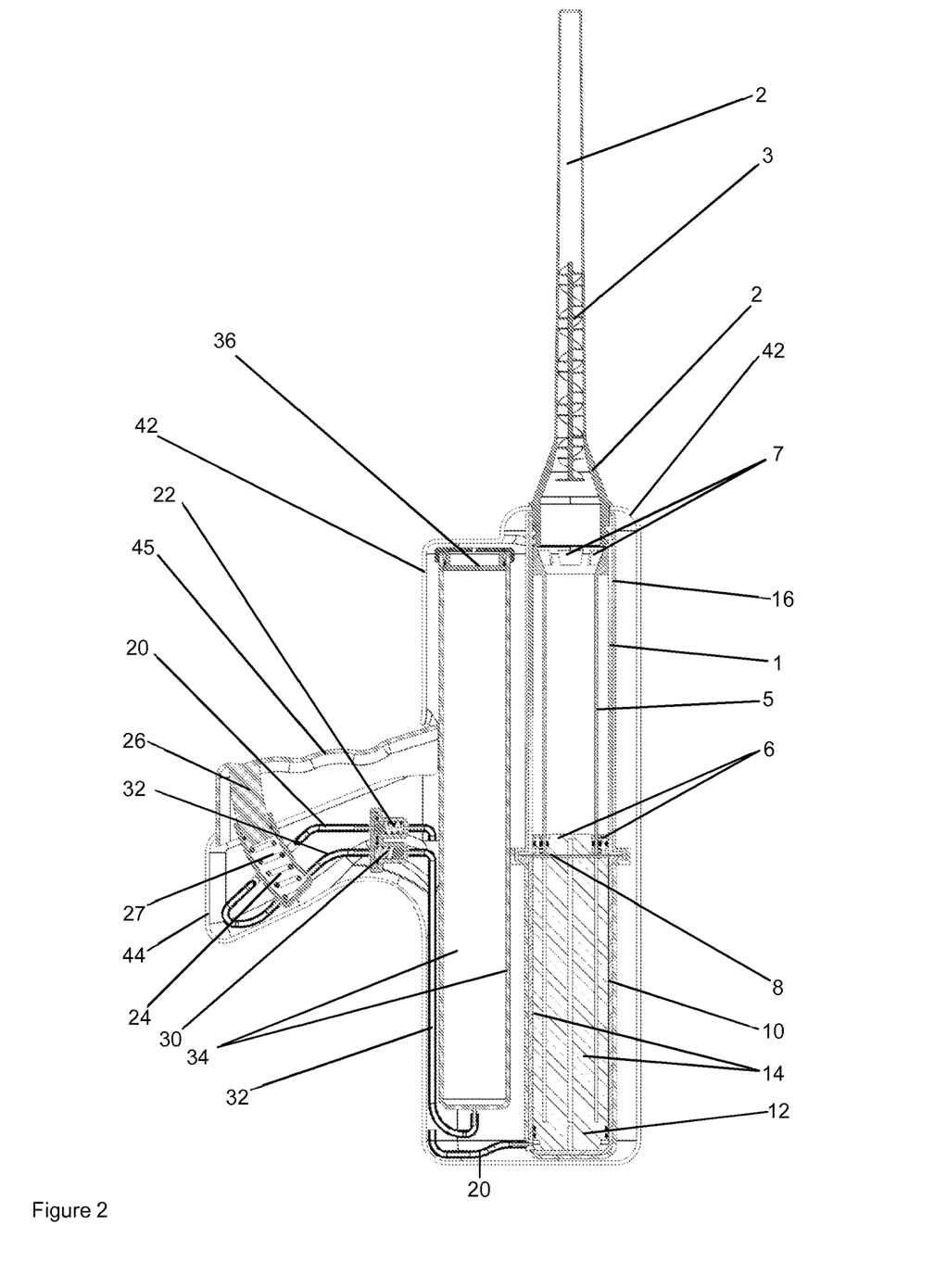
FIG. 2: shows a schematic cross-sectional view of a second paste application system according to the invention.

The two-component cartridge 1 is closed on its rear side by means of a film 8 made of metal-coated plastics, which closes the two-component cartridge 1 in gas-tight manner, when the closure 4 is inserted in the two-component cartridge 1 and closes the openings 7.

A hollow cylinder 10 is placed against the rear side of the two-component cartridge 1 and is closed on the rear side (on the bottom in FIGS. 2 to 6) in pressure-tight manner by means of a plunger 12. The plunger 12 is sealed with respect to the wall of the hollow cylinder 10 by means of seals and is axially mobile in the hollow cylinder 10. The plunger 12 is extended in pestles 14 that comprise recesses or free regions at least in one region, whereby the recesses or free regions are required to be able to propel the pestles 14 into the interior spaces of the cartridge, i.e. to take up the separating wall 5.

The propelled pestles 14 sever the film 8 and drive the feed plungers 6 in the direction of the dispensing tube 2, which expels the content of the two-component cartridge from the interior spaces of the cartridge, presses them into the mixer 3, where the two starting components are mixed with each other, and the mixed paste can be applied by means of the tip of the dispensing tube 2.

For this purpose, the plunger 12 must be driven forward (upward in FIGS. 2 to 6) at a high pressure due to the high viscosity of the starting components and mixed paste and due to the resistance exerted by the static mixer 3. Since the hollow cylinder 10 also consists of a plastic material, the hollow cylinder 10 and the two-component cartridge 1 must be protected from the very strong forces required. For this purpose, the two-component cartridge 1 and the hollow cylinder 10 are surrounded by a pressure container 16 made of metal or a very tough plastic material, such as, e.g., duroplasts, polyamides, polyamide-co-imides, polysulfones, polyketones, and polyetherketones.

The pressure container 16 is capable of taking up a tensile modulus according to EN ISO 527 of more than 1,500 MPa. The pressure container 16 is designed to be made of two parts, whereby the two parts of the pressure container 16 are connected to each other, for example by means of a thread. The pressure container 16 is cylindrical on the inside and is placed, on the outside, against the two-component cartridge 1 and the hollow cylinder 10 or is situated at only a very small distance of maximally 100 µm from the two-component cartridge 1 and the hollow cylinder 10. This ensures that the two-component cartridge 1 and the hollow cylinder 10 are not deformed at all or only to a minor extent during the propulsion of the plunger 12 such that the moving parts, namely the plunger 12, the pestles 14, and the feed plungers 6, do not get lodged and blocked and such that no paste can leak out other than through the dispensing tube 2.

An opening (not shown), through which the air from the gap in the hollow cylinder 10 between the plunger 12 and/or the pestles 14 and the film 8 can escape, can be provided optionally on one side surface in the hollow cylinder 10 and the pressure content 16. By this means, the enclosed gas can be prevented from counteracting the motion of the plunger 12, if applicable.

A manually operable valve 18, by means of which gas can be released from the space between the closed rear wall of the hollow cylinder 10 and the plunger 12, is provided on the rear side of the hollow cylinder 10 and of the pressure container 16. This allows a gas to be released from the hydraulic liquid. For this purpose, it is preferable to arrange the opening for the valve 18 on a curvature (not shown) such that the air or other gas inclusions collect(s) in the curvature and can be released by means of the valve 18, when the paste application system is held with the dispensing tube 2 facing downward.

Moreover, a hydraulic conduit 20 merges into the rear side of the hollow cylinder 10. A non-return valve 22 is arranged in the hydraulic conduit 20. The non-return valve 22 is designed to include a ball that is seated by means of a compression spring, whereby the ball is pressed onto a fitting ball seat by the compression spring in order to close the non-return valve 22. If the liquid contained therein flows in the direction of the hollow cylinder 10 at a sufficient pressure, the non-return valve 22 opens.

The hydraulic conduit 20 merges into an curved (arched) hollow cylinder 24, in which a plunger 26 that is supported such as to be axially mobile and is curved alike is arranged. The plunger 26 is sealed with respect to the internal walls of the curved hollow cylinder 24 through a sealing ring. The plunger 26 ends in a trigger 45 by means of which the plunger 26 can be pushed into and pulled out of the curved hollow cylinder 24 by hand. For this purpose, the trigger 45 is supported such that it can rotate about an axis 60 and/or can be tilted against a housing 42 of the paste application system. When the plunger 26 is pushed into the curved hollow cylinder 24, the liquid present in the hollow cylinder 24 is pressed through the hydraulic conduit 20 and the non-return valve 22 into the hollow cylinder 10. Since the front surface area of the plunger 26 is significantly smaller than the corresponding front surface area of the plunger 12, this produces a transmission ratio. By this means, even a small force exerted by pressing on the plunger 26 can apply a large pressure on the plunger 12 which drives the feed plungers 6 such that very viscous pastes can be expelled and mixed. The curved hollow cylinder 24 has a compression spring 27 arranged in it that restores the trigger 45 and the plunger 26, when the trigger 45 and thus the plunger 26 are pushed in.

The curved hollow cylinder 24 merges, on its front side, in a conduit 32 as well, in which a non-return valve 30 is arranged that is designed like the other non-return valve 22 in the other hydraulic conduit 20. The non-return valve 30 permits the liquid to flow only in the direction of the hollow cylinder 24. The conduits 20, 32, the non-return valves 22, 30, and the connectors must be able to take up the high pressures that occur during operation, without becoming leaky.

On the other side, the conduit 32 merges into a cylindrical liquid container 34 that has a large volume as compared to the second hollow cylinder 24 and is closed, on one side, by means of an axially mobile and sealed plunger 36. The restoration of the plunger 26 by the compression spring 27 generates a negative pressure in the hollow cylinder 24 such that the non-return valve 30 opens and the liquid can flow from the liquid container 34 into the hollow cylinder 24. Accordingly, the plunger 12 is propelled forward in stages in the curved hollow cylinder 10 by multiply triggering the trigger 45, and thus the plunger 26, in the curved hollow cylinder 24.

On the rear side (on the bottom in FIG. 1), an opening 56 is provided in a cap 54 of the liquid container 34 such that no negative pressure can build up between the plunger 36 and the cap 54 and counteract a propulsion of the plunger 36. An inlet valve (not shown), by means of which the liquid container 34 can be filled with liquid, is provided on the front side of the liquid container 34.

The hollow cylinders 10, 24, the liquid container 34, the two-component cartridge 1, the conduits 20, 32, and the non-return valves 22, 30 are arranged in the housing 42 made of plastics. The housing 42 forms a pistol handle 44 allowing the paste application system to be held. The trigger 45 and the inlet valve project from the housing 42 and/or are accessible from outside the housing 42.

Figure 3:
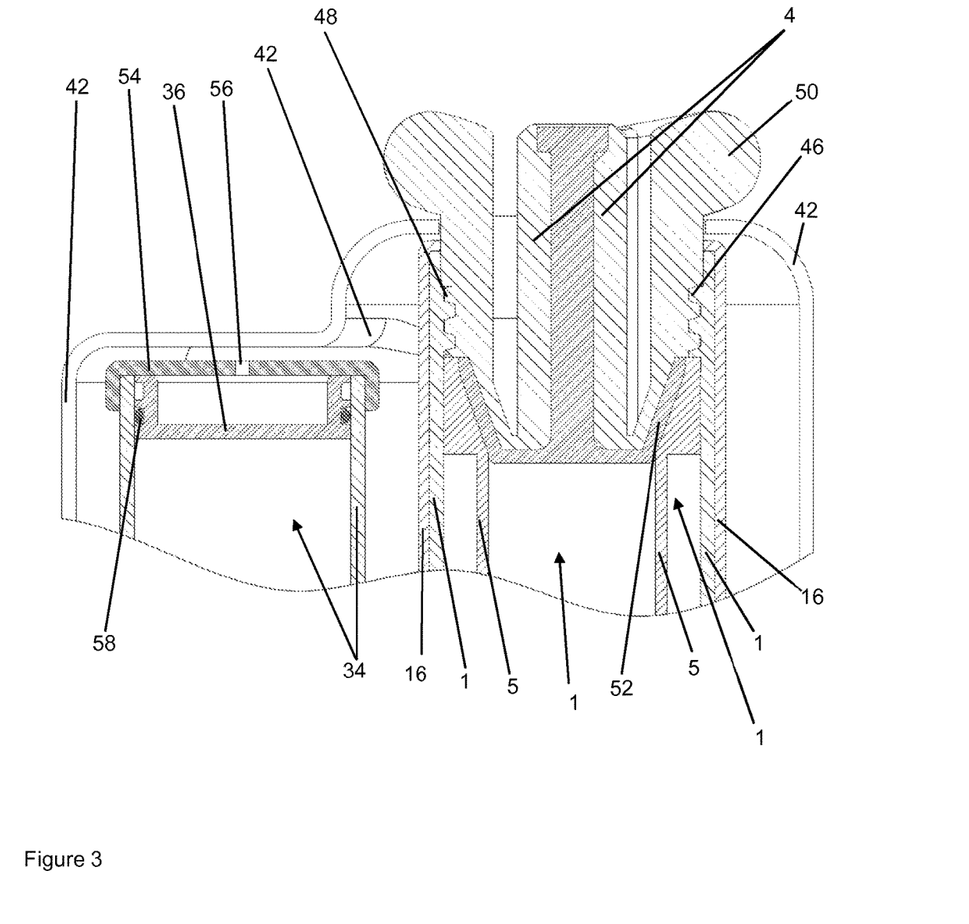
Figure 4:
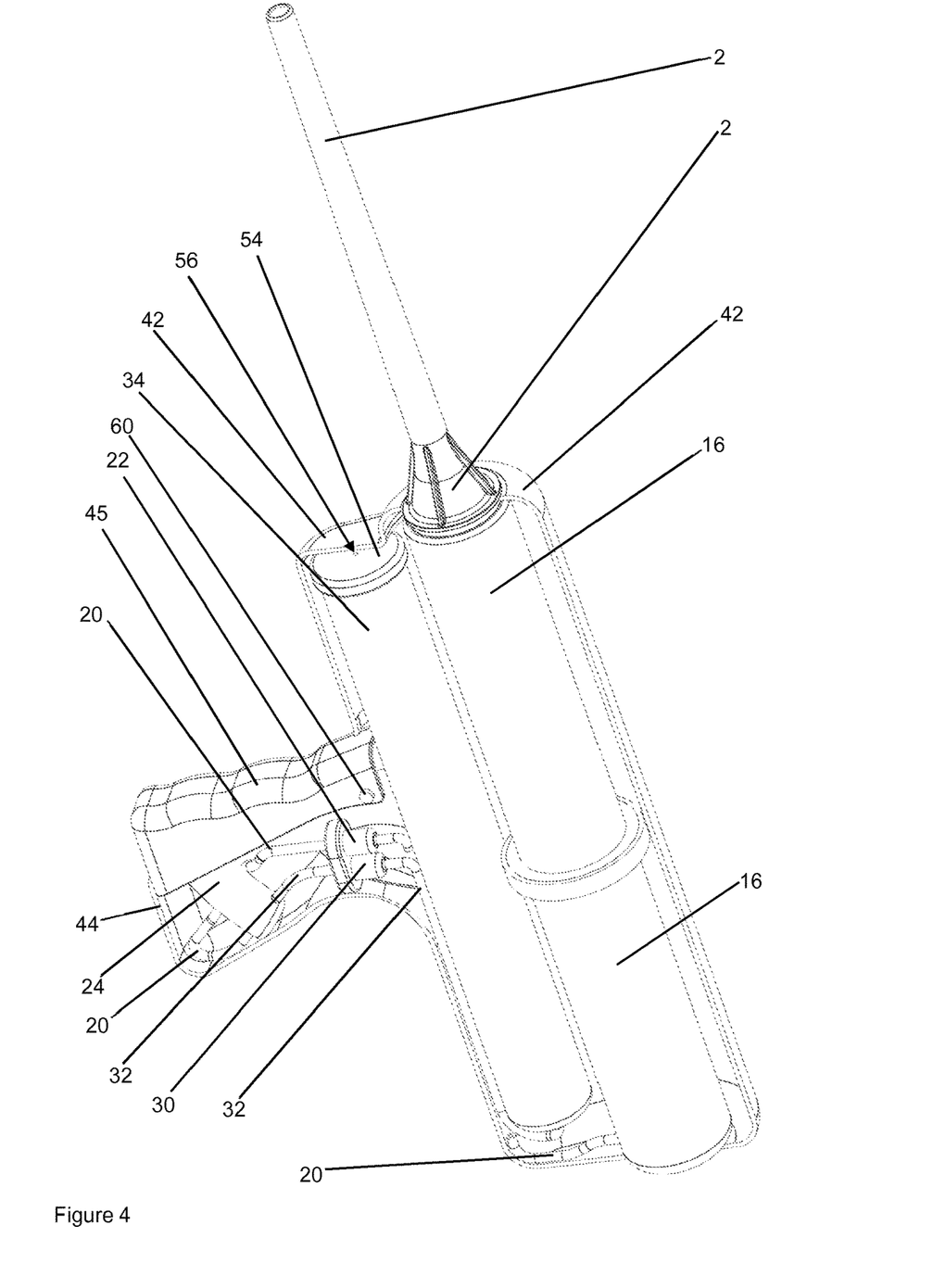
FIG. 4: shows a schematic perspective partial sectional view of the paste application system according to FIGS. 2 and 3 with the housing opened.
Figure 5:
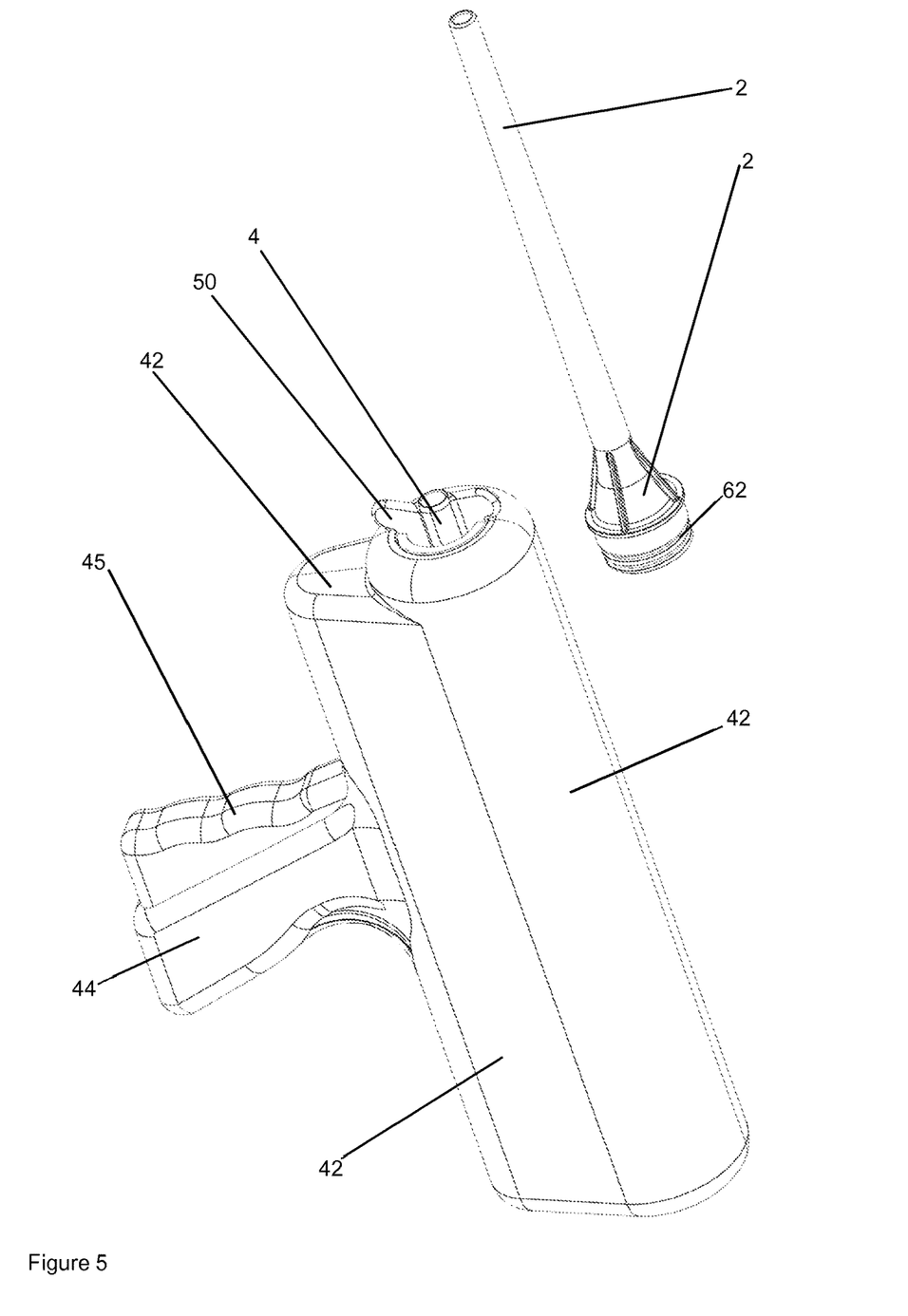
Figure 6:
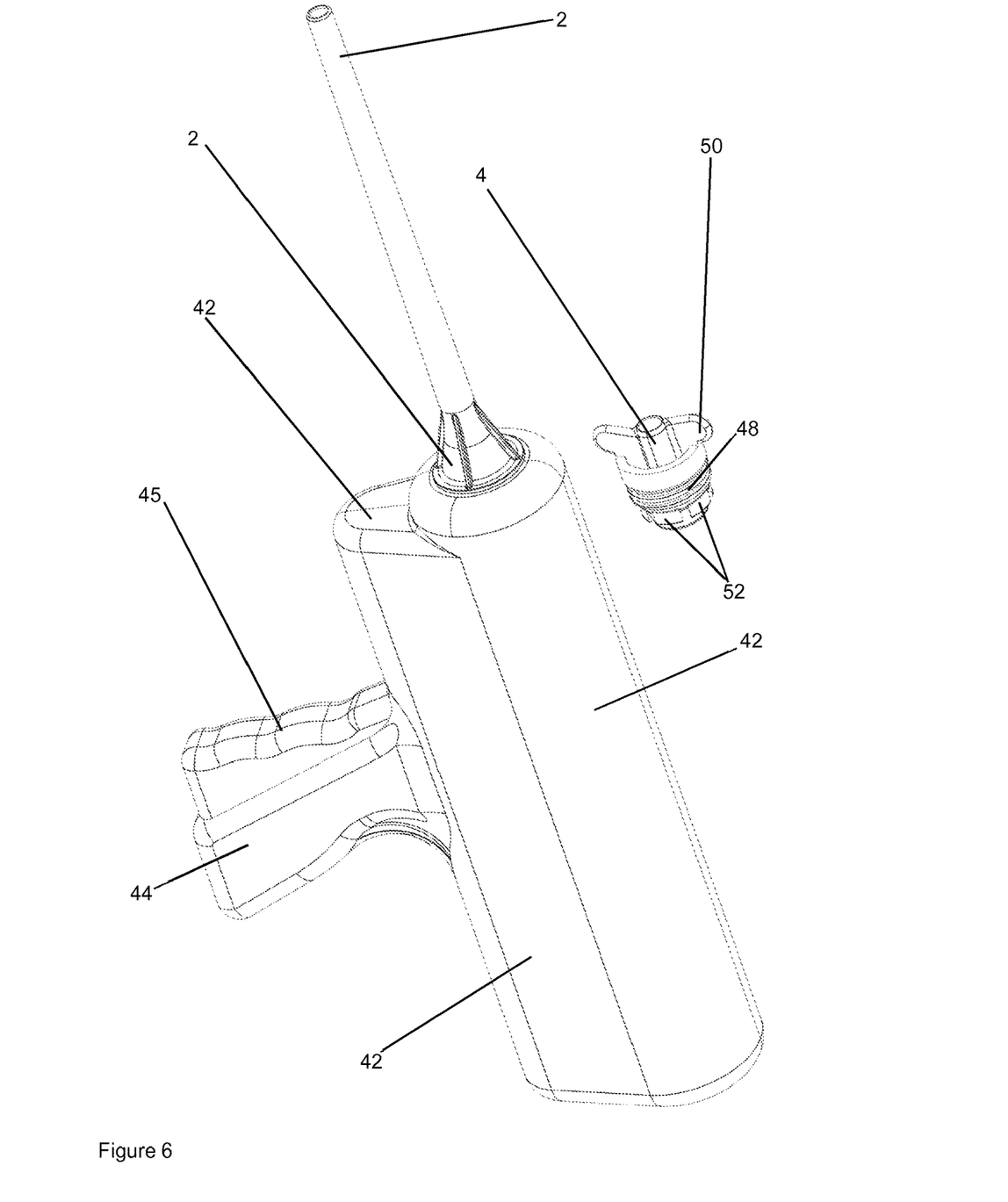

FIG. 3 shows a schematic cross-sectional view of a part of the second paste application system according to the invention. In this context, the paste application system and/or the two-component cartridge 1 is/are closed on the front side by means of a closure 4 that separates the two interior spaces of the cartridge from each other. For this purpose, the two-component cartridge 1 is fitted, on the front side, with an internal thread 46 into which an external thread 48 of the closure 4 is screwed. The closure 4 can be rotated in the way of a screw by means of wings 50 in the way of a wing nut. Sealing surfaces 52 made of an elastic plastic material seal the openings 7 (not shown in FIG. 3) and thus separate the interior spaces of the cartridge from each other. By this means, any inadvertent premature reaction of the two starting components is excluded.

The liquid container 34 is closed on one side by means of a cap 54, in which an opening 56 is provided The purpose of opening 56 is to ensure that no negative pressure can form between the cap 54 and the plunger 36 as volume compensation element that would counteract further motion of the plunger 34 into the inside of the liquid container 34. Advantageously, a tensioned compression spring (not shown) can be arranged between the cap 54 and the plunger 36 in order to support the motion of the plunger 36 into the inside of the liquid container 34.

Figure 7:
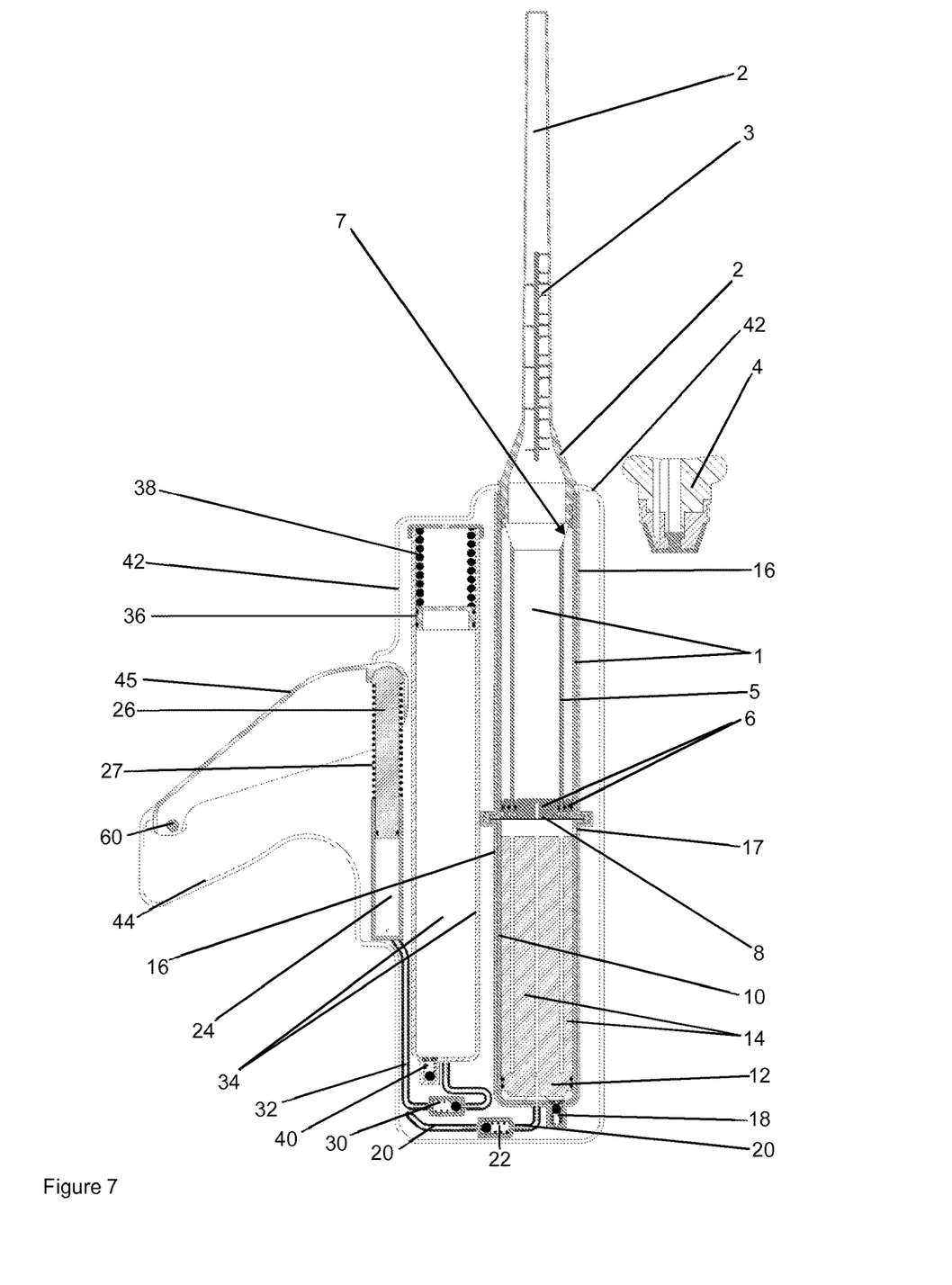
FIG. 7: shows a schematic cross-sectional view of a third paste application system according to the invention.

FIG. 7 shows a schematic cross-sectional view of a third paste application system according to the invention that differs just by a few details from the first two paste application systems. The third paste application system also has a two-component cartridge 1 that contains two pasty starting components (not shown) for the production of a PMMA bone cement in interior spaces of the cartridge that are separated from each other and are arranged coaxially with respect to each other. A dispensing tube 2, in which a static mixer 3 is arranged, is attached on the front side of the two-component cartridge 1. In the storage state of the paste application system, a closure 4 is inserted into the front end (on the top in FIG. 7) of the two-component cartridge 1 instead of the dispensing tube 2.

For separation of the interior spaces of the two-component cartridge 1, a cylindrical tube is provided as a separating wall 5 between the two interior spaces of the cartridge. This results in an outer interior space of the cartridge that is separated from the inner interior space of the cartridge by the cylindrical separating wall 5. The rear-side end (on the bottom in FIG. 7) of the two-component cartridge 1 has two feed plungers 6 arranged in the interior spaces of the cartridge, which are arranged such as to be axially mobile in the interior spaces of the cartridge and are sealed with respect to the bordering walls 5, 1 of the interior spaces of the cartridge by means of sealing rings. The interior spaces of the cartridge are connected to each other by means of openings 7 on the front side (on the top in FIG. 7) such that the interior spaces of the cartridge merge into each other toward the dispensing tube 2. The two-component cartridge 1, the dispensing tube 2, and the separating wall 5 can be made of a plastic material that is chemically resistant to the content of the cartridge.

The two-component cartridge 1 is closed on its rear side by means of a film 8 made of plastics, which closes the two-component cartridge 1 in gas-tight manner, when the closure 4 is inserted in the two-component cartridge 1 and closes the openings 7.

A hollow cylinder 10 is placed against the rear side of the two-component cartridge 1 and is closed on the rear side (on the bottom in FIG. 7) in pressure-tight manner by means of a plunger 12. The plunger 12 is sealed with respect to the wall of the hollow cylinder 10 by means of seals and is axially mobile in the hollow cylinder 10. The plunger 12 is extended in pestles 14 that comprise recesses or free regions at least in one region, whereby the recesses or free regions are required to be able to propel the pestles 14 into the interior spaces of the cartridge, i.e. to take up the separating wall 5.

The propelled pestles 14 sever the film 8 and drive the feed plungers 6 in the direction of the dispensing tube 2, which expels the content of the two-component cartridge from the interior spaces of the cartridge, presses them into the mixer 3, where the two starting components are mixed with each other, and the mixed paste can be applied by means of the tip of the dispensing tube 2.

For this purpose, the plunger 12 must be driven forward (upward in FIG. 1) at a high pressure due to the high viscosity of the starting components and mixed paste and due to the resistance exerted by the static mixer 3. Since the hollow cylinder 10 also consists of a plastic material, the hollow cylinder 10 and the two-component cartridge 1 must be protected from the very strong forces that occur in this context. For this purpose, the two-component cartridge 1 and the hollow cylinder 10 are surrounded by a pressure container 16 made of metal or a very tough plastic material, such as, e.g., duroplasts, polyamides, polyamide-co-imides, polysulfones, polyketones, and polyetherketones. The pressure container 16 is capable of taking up a tensile modulus according to EN ISO 527 of more than 1,500 MPa. The pressure container 16 is designed to be made of two parts, whereby the two parts of the pressure container 16 are connected to each other, for example by means of a thread or a flange having a flange clasp. The pressure container 16 is cylindrical on the inside and is placed, on the outside, against the two-component cartridge 1 and the hollow cylinder 10 or is situated at only a very small distance of maximally 100 μm from the two-component cartridge 1 and the hollow cylinder 10. This ensures that the two-component cartridge 1 and the hollow cylinder 10 are not deformed at all or only to a minor extent during the propulsion of the plunger 12 such that the moving parts, namely the plunger 12, the pestles 14, and the feed plungers 6, do not get lodged and blocked and such that no paste can leak out other than through the dispensing tube 2.

Openings 17, through which the air from the gap in the hollow cylinder 10 between the plunger 12 and/or the pestles 14 and the film 8 can escape, are provided on one side surface in the hollow cylinder 10 and the pressure content 16. By this means, the enclosed gas is to be prevented from counteracting the motion of the plunger 12. A manually operable valve 18, by means of which gas can be released from the space between the closed rear wall of the hollow cylinder 10 and the plunger 12, is provided on the rear side of the hollow cylinder 10 and of the pressure container 16. This allows a gas to be released from the hydraulic liquid. For this purpose, it is preferable to arrange the opening for the valve 18 on a curvature (not shown) such that the air or other gas inclusions collect(s) in the curvature and can be released by means of the valve 18, when the paste application system is held with the dispensing tube 2 facing downward. The valve 18 can also be used as a safety valve that opens when the pressure becomes excessive.

Moreover, a hydraulic conduit 20 merges into the rear side of the hollow cylinder 10. A non-return valve 22 is arranged in the hydraulic conduit 20. The non-return valve 22 is designed to include a ball that is seated by means of a compression spring, whereby the ball is pressed onto a fitting ball seat by the compression spring in order to close the non-return valve 22. If the liquid contained therein flows in the direction of the hollow cylinder 10 at a sufficient pressure, the non-return valve 22 opens.

The hydraulic conduit 20 merges into a hollow cylinder 24, in which a plunger 26 that is supported such as to be axially mobile is arranged. The plunger 26 is sealed with respect to the internal walls of the hollow cylinder 24 through a sealing ring. The plunger 26 ends on a trigger 45 by means of which the plunger 26 can be pushed into and pulled out of the hollow cylinder 24 by hand. For this purpose, the trigger 45 is supported such that it can rotate about an axis 60 and/or can be tilted against a housing 42 of the paste application system. When the plunger 26 is pushed into the hollow cylinder 24, the liquid present in the hollow cylinder 24 is pressed through the hydraulic conduit 20 and the non-return valve 22 into the hollow cylinder 10. Since the front surface area of the plunger 26 is significantly smaller than the corresponding front surface area of the plunger 12 (the front surface area of the plunger 26 is smaller than the front surface area of the plunger 12 by at least a factor of ten or by at least a factor of twenty), this produces a transmission ratio. By this means, even a small force exerted by pressing on the plunger 26 can apply a large pressure on the plunger 12 which drives the feed plungers 6 such that very viscous pastes can be expelled and mixed. The plunger 26 is supported, by means of a compression spring 27, against the hollow cylinder 24, whereby the compression spring 27 restores the trigger 45 and the plunger 26, when the trigger 45 and thus the plunger 26 are pushed in.

The hollow cylinder 24 merges, on its front side, in a conduit 32 as well, in which a non-return valve 30 is arranged that is designed like the other non-return valve 22 in the other hydraulic conduit 20. The non-return valve 30 permits the liquid to flow only in the direction of the hollow cylinder 24. The conduits 20, 32, the non-return valves 22, 30, and the connectors must be able to take up the high pressures that occur during operation, without becoming leaky.

On the other side, the conduit 32 merges into a cylindrical liquid container 34 that has a large volume as compared to the second hollow cylinder 24 and is closed, on one side, by means of an axially mobile and sealed plunger 36. The plunger 36 is tensioned by means of a compression spring 38 such that the liquid can be easily pushed and/or drawn from the liquid container 34 into the conduit 32 and into the hollow cylinder 24 by the plunger 36. The restoration of the plunger 26 by the compression spring 27 generates a negative pressure in the hollow cylinder 24 such that the non-return valve 30 opens and the liquid can flow from the liquid container 34 into the hollow cylinder 24.

Accordingly, the plunger 12 is propelled forward in stages in hollow cylinder 10 by multiply pumping and/or by multiply pushing and retracting the plunger 26 in the hollow cylinder 24.

On the rear side (on the bottom in FIG. 7), an opening is provided in a cap of the liquid container 34 such that no negative pressure can build up between the plunger 36 and the cap and counteract a propulsion of the plunger 36. A non-return valve 40, by means of which the liquid container 34 can be filled with liquid, is provided on the front side of the liquid container 34.

The hollow cylinders 10, 24, the liquid container 34, the two-component cartridge 1, the conduits 20, 32, and the non-return valves 22, 30 are arranged in the housing 42 made of plastics. The housing 42 forms a pistol handle 44 allowing the paste application system to be held. The handle 28, the valve 18, and the valve 14 project from the housing 42 and/or are accessible from outside the housing 42.

The features of the invention disclosed in the preceding description and in the claims, figures, and exemplary embodiments, can be essential for the implementation of the various embodiments of the invention both alone and in any combination.

LIST OF REFERENCE NUMBERS

1 Two-component cartridge
2 Dispensing tube
3 Static mixer
4 Closure
5 Separating wall
6 Feed plunger
7 Opening of the two-component cartridge
8 Film
10 Hollow cylinder
12 Plunger
14 Pestle
16 Pressure container
17 Opening
18 Valve
20 Hydraulic conduit
22 Non-return valve
24 Hollow cylinder
26 Plunger
27 Spring
28 Handle
30 Non-return valve
32 Conduit
34 Liquid container
36 Plunger
38 Spring
40 Non-return valve
42 Housing
44 Pistol handle
45 Trigger
46 Internal thread
48 External thread
50 Wing
52 Seal
54 Cap
56 Opening
58 Seal
60 Axis

The invention claimed is:

1. A paste application system for storing two starting components, for mixing the starting components to form a paste, and for applying the paste, said paste application system comprising:
(a) a two-component cartridge with two axially shiftable feed plungers;
(b) a first cylinder having an open front face and an at least partially closed rear face, the first cylinder containing within an axially mobile first plunger having two axially mobile pestles, wherein the open front face of the first cylinder adjoins a rear of the two-component cartridge;
(c) a second cylinder containing a manually shiftable second plunger;
(d) a liquid container connected or connectable to the second cylinder by a first liquid conduit and a first non-return valve, the second cylinder, in turn, being connected or connectable to the first cylinder by a second liquid conduit and a second non-return value;
whereby the two-component cartridge and the first cylinder are arranged in a pressure container;
whereby a space for liquid and allowing flow of liquid is formed or formable in the paste application system by connections between the liquid container, the first liquid conduit, the second liquid conduit, the first non-return valve, the second non-return valve, internal space of the first cylinder and internal space of the second cylinder; and
whereby a liquid is present in said space or can be filled into said space.

2. Paste application system according to claim 1, wherein the paste application system comprises a dispensing tube with an integrated static mixer that is arranged on or can be attached to the end of the two-component cartridge opposite from the feed plungers.

3. Paste application system according to claim 1, wherein the pressure container has a tensile modulus of more than 1,500 MPa.

4. Paste application system according to claim 1, wherein the liquid container comprises a volume compensation element.

5. Paste application system according to claim 4, wherein a tensioned compression spring is arranged on the side of the volume compensation element of the liquid container that faces away from the region for the liquid, and pushes the volume compensation element in the direction of the liquid container, and presses liquid through the first conduit and through the first non-return valve to the second cylinder.

6. Paste application system according to claim 1, wherein an opening is provided in the jacket surface of the pressure container that is connected, in gas-permeable manner, to an opening in the first cylinder such that the space between the two-component cartridge and the axially mobile pestles is connected to the ambient atmosphere in gas-permeable manner.

7. Paste application system according to claim 1, wherein at least one closable opening is provided for adding liquid that is connected to the space for liquid, whereby the opening for adding liquid is optionally arranged on the liquid container.

8. Paste application system according to claim 1, wherein at least one closable ventilation opening is provided that is connected to the space for liquid.

9. Paste application system according to claim 8, wherein the closed rear face of the first cylinder is curved and the closable ventilation opening is arranged in the curvature.

10. Paste application system according to claim 1, wherein the two-component cartridge, the first cylinder, and the second cylinder are arranged in a housing, whereby it is optional to have the first conduit, the first non-return valve, the second conduit, and the second non-return valve also arranged in said housing.

11. Paste application system according to claim 1, wherein a liquid is present in the space for liquid, and the liquid is without any visually recognisable gas bubbles and/or in the liquid contains less than 5% by volume of gas.

12. Paste application system according to claim 1, wherein the distances between the pressure container and an external wall of the two-component cartridge and between the pressure container and an external wall of the first cylinder are smaller than 100 µm.

13. Paste application system according to claim 1, wherein the pressure container is made from a material selected from aluminium, aluminium alloys and high-performance plastics.

14. Paste application system according to claim 1, wherein
a third conduit and a third valve, which can be closed reversibly by hand, connect the first cylinder to the liquid container.

15. Paste application system according to claim 1, wherein a surface area ratio of a front face of the first plunger and a front face of the second plunger is at least 10 to 1.

16. Paste application system according to claim 1, wherein the two-component cartridge comprises two interior spaces of the cartridge, whereby the feed plungers are axially mobile in the interior spaces of the cartridge, whereby it is optional that a first interior space of the cartridge surrounds a second interior space of the cartridge in coaxial manner.

17. Paste application system according to claim 16, wherein the interior spaces of the cartridge are separated or separable on the side opposite from the feed plungers by a manually detachable closure, whereby the closure optionally is or can be screwed into an internal thread on the front side of the two-component cartridge.

18. Paste application system according to claim 1, wherein the pressure container comprises at least one opening on a front face, whereby it is optional to have at least one valve for gas release arranged on one of the openings.

19. A method for mixing and dispensing a paste, comprising:
(a) providing a paste application system according to claim 1;
(b) guiding a liquid from the liquid container through the first non-return valve and the first conduit into the second cylinder;
(c) subsequently, pushing the liquid from the second cylinder through the second non-return valve and the second conduit into the first cylinder by applying a manual pressure on the second plunger in the second cylinder, whereby the liquid pressed into the first cylinder pushes the first plunger, which has a larger face surface to the liquid as compared to the second plunger, in the direction of the two-component cartridge, whereby at least the two feed plungers that are axially shiftable in the two-component cartridge are propelled by the first plunger or by the pestles attached to the first plunger in at least two interior spaces of the two-component cartridge, whereby material is expelled from the two-component cartridge and is subsequently mixed and is applied after the mixing.

20. Method according to claim 19, wherein the forces that occur when the liquid is pressed into the first cylinder and when the first plunger and the feed plungers are propelled in the two-component cartridge are taken up by the pressure container.

21. Method according to claim 19, wherein the second cylinder is filled repeatedly with the liquid from the liquid container by restoring the second plunger, whereby the restoration of the second plunger optionally is effected by a compression spring that gets tensioned when the second plunger is being pushed in, or by any other restoring element.

22. Method according to claim 19, wherein the first non-return valve is opened and the second non-return valve is closed when the liquid is guided from the liquid container into the second cylinder, and the first non-return valve is closed and the second non-return valve is opened when the liquid is pressed from the second cylinder into the first cylinder.

* * * * *